United States Patent [19]

Civin

[11] Patent Number: 5,130,144
[45] Date of Patent: Jul. 14, 1992

[54] HUMAN STEM CELLS AND MONOCLONAL ANTIBODIES

[75] Inventor: Curt I. Civin, Baltimore, Md.

[73] Assignee: The Johns Hopkins University, Baltimore, Md.

[21] Appl. No.: 673,721

[22] Filed: Mar. 22, 1991

Related U.S. Application Data

[62] Division of Ser. No. 580,337, Sep. 7, 1990, which is a division of Ser. No. 55,942, Jun. 1, 1987, Pat. No. 4,965,204, which is a division of Ser. No. 670,740, Feb. 6, 1984, Pat. No. 4,714,680.

[51] Int. Cl.$^5$ .................... A61K 35/28; C12N 5/08
[52] U.S. Cl. .................... 424/577; 435/240.2
[58] Field of Search ............ 435/2, 240.2; 604/4; 424/577

[56] References Cited

U.S. PATENT DOCUMENTS

| | | | |
|---|---|---|---|
| 4,364,932 | 12/1982 | Kung et al. | 530/387 |
| 4,364,937 | 12/1982 | Kung et al. | 530/387 |
| 4,381,292 | 4/1983 | Bieber et al. | 424/1.1 |
| 4,381,295 | 4/1983 | Kung et al. | 530/387 |
| 4,443,427 | 4/1984 | Reinherz et al. | 424/1.1 |
| 4,582,797 | 4/1986 | Trowbridge et al. | 530/387 |
| 4,624,925 | 11/1986 | Kung et al. | 435/240.27 |
| 4,710,457 | 12/1987 | Dupont et al. | 435/7.24 |

OTHER PUBLICATIONS

Preschel et al., "M7 Cluster Rept: CD34", ed. Knapp, at the Fourth Int'l Workshop and Conference on Human Leucocyte (1989), p. 817.
Civin et al., "M7.1 Rept on the CD34 Cluster Workshop", ed. Knapp, at the Fourth Int'l Workshop and Conference on Human Leucocyte (1989), p. 818.
Lansdrop et al., "M7.2 CD34 Epitopes", ed. Knapp, at the Fourth Int'l Workshop and Conference on Human Leucocyte (1989), p. 826.
Molgaard et al., "M7.3 Molecular Characterization of Human and Murine CD34", ed, Knapp, at the Fourth Int'l Workshop and Conference on Human Leucocyte (1989), p. 827.
Civin et al., "Antigenic Analysis of Hematopoiesis III. A Hematopoietic Progenitor Cell Surface Antigen Defined by a Monoclonal Antibody Raised Against KG-1a Cells", J. Immunology 133:157-165 (1984).
Civin et al., "Cell Surface Antigens of Human Myeloid Cells", (1982) Exp. Hematol. 10:129 (abstract).
Civin et al., "Characterization of Four Monoclonal Antibodies Reactive with Human Cell Subsets", Blood, 60(5):95a (abstract).
Civin et al., "Cell Surface Antigens by Four Monoclonal Antibodies Raised Against KG-1a Cells", Hybridoma, 2:125a (abstract).
Brovall et al., "Identification and Partially Characterization of Two Human Potential Hematopoietic Differentiation Antigens" Exp. Hematol. 11:(Supp.) 199 (abstract).
Civin et al., "Diagnostic and Prognostic Utility of Cell Surface Markers In Acute Non-Lymphocytic Leukemia" (ANLL), Exp. Hematol. 11:(Supp.)84.
Strauss et al., "MY-10, A Human Hematopoietic Progenitor Cell Surface Antigen Identified by a Monoclonal Antibody" Exp. Hematol. 11:205 (abstract).
Strauss, et al. "MY-10 Antigen is Lost at the CFU-E Stage During Erythroid Progenitor Cell Maturation", (1984) I.S.E.H. (Abstract).
Leary, et al., "Single Cell Origin of Human Multilineage Colonies", (1984) I.S.E.H. (Abstract).
Bodger, et al., "Surface Antigenic Determinants on Human Pluripotent and Unipotent Hematopoietic Progenitor Cells", (1983) Blood, 61:1006-1010.
Bodger, et al., "A Monoclonal Antibody Specific for Immature Human Hemopoietic Cells and T Lineage Cells", (1981) J. Immunology, 127:2269-2274.
Nadler et al., "Diagnosis and Treatment of Human Leukemias and Lymphomas Utilizing Monoclonal Antibodies" Prog. Hematol., 12:187-225.
Winchester, et al., "Expressin of Ia-like antigen molecules on human granulocytes during early phases of differentiation", Proc. Natl. Acad. Sci. USA 74:4012-4016 (1977).
Stashenko, et al., "Characterization of a Human B Lymphocyte-Specific Antigen" J. Immunology, 125:1678-1685 (1980).
Reinherz, et al., "Regulation of the Immune Response—Inducer and Suppresoor T-Lymphocyte Subsets in Human Beings" (1980) N. Engl. J. Med. 303:370.
Ritz, et al., "A Monoclonal Antibody to Human Acute Lymphoblastic Leukaemia Antigen" Nature 283:583-585.

Primary Examiner—John Doll
Assistant Examiner—George C. Elliott
Attorney, Agent, or Firm—Banner, Birch, McKie & Beckett

[57] ABSTRACT

Monoclonal antibodies that recognize a stage-specifc antigen on immature human marrow cells are provided. These antibodies are useful in methods of isolating cell suspensions from human blood and marrow that can be employed in bone marrow transplantation. Cell suspensions containing human pluripotent lympho-hematopoietic stem cells are also provided, as well as theraputic methods employing the cell suspensions.

4 Claims, No Drawings

HUMAN STEM CELLS AND MONOCLONAL ANTIBODIES

This application is a divisional application of U.S. Ser. No. 580,337, filed Sep. 7, 1990, which is a divisional of U.S. Ser. No. 055,942 filed Jun. 1, 1987 now issued as U.S. Pat. No. 4,965,204, which is a divisional of U.S. Ser. No. 670,740, filed Feb. 6, 1984, now issued as U.S. Pat. No. 4,714,680.

TECHNICAL FIELD

The present invention is directed to cell populations useful in bone marrow transplantation, as well as immortal cells producing monoclonal antibodies to human stem cells.

BACKGROUND OF THE INVENTION

Bone marrow transplantation is an effective therapy for an increasing number of diseases. Graft Versus Host Disease (GVHD), however, limits bone marrow transplantation to recipients with HLA-matched sibling donors. Even then, approximately half of the allogenic bone marrow transplantation recipients develop GVHD. Current therapy for GVHD is imperfect and the disease can be disfiguring and/or lethal. Thus, risk of GVHD restricts the use of bone marrow transplantation to patients with otherwise fatal diseases, such as malignancies, severe aplastic anemia, and congenital immunodeficiency states. Less than 1000 bone marrow transplantations per year are currently performed in the United States. Many other patients have diseases that might be treated by marrow cell transplantation (such as sickle cell anemia) if GVHD were not such a serious risk.

The potential benefits from expanded use of bone marrow transplantation have stimulated research on the cause and prevention of GVHD. It has been shown that donor T lymphocytes causes GVHD in animals. Removal of T lymphocytes from donor marrow inocula ("grafts") prevented the subsequent development of GVHD in mice, dogs and monkeys. Similar trials in humans with monoclonal antibodies against human T lymphocytes are now in progress. Preliminary results, however, suggest only attenuation of GVHD, not a cure. Similar results have been achieved with E-rosette and soybean lectin depletion of T lymphocytes. Another approach under investigation is the use of anti-T lymphocyte monoclonal antibodies conjugated to toxins, such as ricin.

As of yet, however, GVHD has not been prevented or cured in bone marrow recipients. A continuing need exists, therefore, for new methods of combatting Graft Versus Host Disease.

Donors of bone marrow are also faced with undesirable procedures and risks. The current procedures for harvesting bone marrow are expensive and painful. Furthermore, the current donation procedure is accompanied by the risks associated with anethesia, analgesia, blood transfusion and possible infection. It would be desirable, therefore, to improve the current method of harvesting marrow from donors.

SUMMARY OF THE INVENTION

It is an object of the present invention to reduce or eliminate GVHD associated with bone marrow transplantation.

Another object of the present invention is to provide monoclonal antibodies that selectively bind immature bone marrow cells.

A further object of the present invention is to provide a method for preparing a cell population useful for stem cell transplantation that is enriched in immature marrow cells and substantially free of mature myeloid and lymphoid cells.

Yet another object of the present invention is to provide a method of collecting donations useful for stem cell transplantation that avoids the disadvantages of conventional marrow harvesting techniques.

Still another object of the present invention is to provide a theraputic method of transplanting stem cells that can extend the use of stem cell transplantation to the treatment of non-fatal diseases.

These and other objects of the present invention are achieved by one or more of the following embodiments.

In one embodiment, the present invention provides a monoclonal antibody that recognizes an antigen on human pluripotent lymphohematopoietic stem cells, but does not recognize an antigen on normal, human mature lymphoid and myeloid cells.

The present invention also provides a monoclonal antibody to normal, immature human marrow cells that is stage-specific and not lineage dependent, said antibody (a) recognizing an antigen on normal, human blood or bone marrow (i) colony-forming cells for granulocytes/monocytes (CFC-GM), (ii) colony-forming cells for erythrocytes (BFU-E), (iii) colony-forming cells for eosinophils (CFC-Eo), (iv) multipotent colony-forming cells (CFC-GEMM), and (v) immature lymphoid precursor cells; (b) recognizing an antigen on a maximum of about 5% normal, human marrow cells and a maximum of about 1% normal, human peripheral blood cells; and (c) not recognizing an antigen on normal, mature human myeloid and lymphoid cells.

The present invention also provides a monoclonal antibody that recognizes the antigen recognized by the antibody produced by the hybridoma deposited under ATCC Accession No. HB-8483.

The present invention further provides immortal cell lines that produce the above antibodies.

In still another embodiment, the present invention provides a method of producing a population of human cells containing pluripotent lympho-hematopoietic stem cells comprising: (a) providing a cell suspension from human tissue, said tissue selected from the group consisting of marrow and blood; (b) contacting said cell suspension with a monoclonal antibody to immature human marrow cells that is stage-specific and not lineage dependent, said antibody recognizes an antigen on human pluripotent lympho-hematopoietic stem cells, but does not recognize an antigen on mature, human myeloid and lymphoid cells; and (c) separating and recovering from said cell suspension the cells bound by said antibody.

In a further embodiment, the present invention provides a method of providing a population of human cells containing pluripotent lympho-hematopoietic stem cells comprising: (a) providing a cell suspension from human tissue, said tissue selected from the group consisting of marrow and blood; (b) contacting said cell suspension with a solid-phase linked monoclonal antibody to immature human marrow cells that is stage-specific and not lineage dependent, said antibody recognizes an antigen on human pluripotent lympho-hematopoietic stem cells, but does not recognize an antigen on mature human myeloid and lymphoid cells; and (c) separating unbound cells from solid-phase linked monoclonal antibody after said contacting; and (d) recovering bound cells from said solid-phase linked monoclonal antibody after separating said unbound cells.

Yet another embodiment of the present invention provides a suspension of human cells comprising pluripotent lympho-hematopoietic stem cells substantially free of mature lymphoid and myeloid cells, as well as therapeutic methods employing such a cell suspension.

DETAILED DESCRIPTION OF THE INVENTION

The present invention provides a significant advance in the art of bone marrow transplantation. An antigen has been discovered that is expressed on immature, normal human marrow cells, including pluripotent lympho-hematopoietic stem cells (stem cells). Stem cells have the ability to restore, when transplanted, the production of hematopoietic and lymphoid cells to a patient who has lost such produciton due to, for example, radiation therapy. Unlike other antigens to which monoclonal antibodies have been developed, the antigen disclosed herein is not expressed by mature myeloid or lymphoid cells, yet appears on all colony-forming myeloid progenitors assayed to date. The newly discovered antigen is a stage-specific antigen that appears on bone marrow cells desirable for use in a bone marrow transplant, yet is not expressed on the more mature lymphoid cells which have been implicated as the cause of Graft Versus Host Disease. Furthermore, it has been found that the newly discovered antigen is not expressed on the peripheral blood cells that would be unnecessary or unwanted for stem cell transplantation, thus permitting the isolation of stem cells from human blood. The present invention also provides monoclonal antibodies which facilitate the isolation of the desired cells and make possible improved theraputic techniques that significantly contribute to the understanding and prevention of Graft Versus Host Disease. The isolated stem cells can also be employed to produce panels of monoclonal antibodies to stem cells.

The newly discovered antigen has been designated My-10. This antigen was identified by a monoclonal antibody raised against the KG-1a human leukemic cell line. The KG-1a cell line arose as a spontaneous tissue culture variant from the KG-1 myeloblastic leukemic cell line derived from a patient with non-lymphocytic leukemia. See Koeffler et al., (1978) *Science* 200: 1153; Koeffler et al., (1980) *Blood* 56: 265. Both the KG-1a and KG-1 leukemic cell lines are available from Dr. David Golde, at the University of California, Los Angeles.

The My-10 antigen is expressed as a cell-surface antigen on the KG-1a and KG-1 cell lines. The antigen is immunoprecipitated from extracts of these cell lines as a protein of approximately 115 kD (kilodalton) apparent molecular weight. The My-10 antigen is also expressed on a number of fresh acute leukemia (both lymphoid and non-lymphoid) blast cell specimens.

My-10 is expressed on very few normal human peripheral blood cells or marrow cells. Assays detect My-10 antigen on a maximum of about 5% of the normal human marrow cells and a maximum of about 1% of normal human peripheral blood cells. Various assay techniques have been employed to test for the presence of the My-10 antigen and those techniques have not detected any appreciable number (i.e., not significantly above background) of normal, mature human myeloid and lymphoid cells in My-10-positive populations. Indeed, the ability to detect My-10 antigen diminishes rapidly as blast cells differentiate into mature myeloid and lymphoid cells.

The indirect immune adherance ("panning") technique is an appropriate assay to separate the rare My-10-positive normal human bone marrow cells from the predominant My-10 -negative marrow cells. Over 50% of the My-10-positive marrow cells found by this technique are blast cells of heterogeneous morphology. Only rarely are progranulocytes, promonocytes and more mature granulocytic or monocytic cells found in the My-10-positive cell fraction. Confirming results with even higher purity of isolated My-10-positive cells are achieved with immune rosetting and fluorescence-activated cell sorting (FACS).

The My-10 antigen is expressed on colony-forming cells of all marrow or blood cells lineages tested to date. For example, over 90% of the colony-forming cells-granulocyte/monocyte (CFC-GM) are isolated in the My-10-positive fraction obtained by panning marrow cells. Like CFC-GM, the colony-forming cells for pure colonies of eosinophils (CFC-Eo) are My-10-positive. Large erythroid colony-forming progenitor cells (BFU-E) are also almost uniformly My-10-positive. Mixed multipotent colony-forming cells (CFC-GEMM) also express the cell surface antigen, My-10. Only about half of the presumably more differentiated progenitors of smaller erythroid colonies ("CFU-E-like") were in the My-10-positive population obtained by panning. Erythroid cells more mature than erythroid blasts are uniformly My-10-negative. These results indicate that the cell surface My-10 expression decreases sharply between the large, immature BFU-E stage and the latter stages of erythroid maturation.

My-10 antigen is also found on immature lymphoid precursor cells. These immature lymphoid cells can be identified, for example, by detecting the presence of nuclear terminal deoxynucleotidyl transferase (TdT) as described by Bollum, (1979) *Blood* 54: 1203. Approximately 5-30% of My-10-positive marrow cells have been found to be TdT-positive in several experiments. Less than 1% of the My-10-negative marrow cells were TdT-positive.

Thus, My-10 is a stage-specific antigen that is detectable on normal, human marrow or blood colony-forming cells and immature lymphoid precursor cells, but not on normal, mature human lymphoid and myeloid cells. The antigen is not lineage dependent, but appears on a spectrum of lympho-hematopoietic progenitor cells.

Anti-My-10 anitibodies are extremely useful in hematopoietic research because anti-My-10 antibodies label the lympho-hematopoietic progenitor cell subset more specifically that any previously described antibody. An anti-My-10 antibody recognizes an antigen on the smallest percentage of more mature marrow cells reported and allows the isolation of relatively pure populations of immature lympho-hematopoietic cells in a single step. My-10-positive marrow cells recovered with anti-My-10 antibody can be an appropriate control normal cell population to compare with leukemic blast cells and to use in studies on the mechanisms of action of cells, factors and genes which regulate hematopoietic cell poliferation and differentiation. The near 100% recovery of most in vitro colony-forming cells in the My-10-positive marrow cell subpopulation indicates that My- 10-negative accessory cells are not necessary for the growth and differentiation of these progenitor cells. Anti-My-10 antibodies also have important theraputic application because they allow the recovery of hematopoietic stem cell-enriched, mature lymphocyte-depleted cell populations for use in human stem cell transplantation.

Anti-My-10 antibody is unique in that it recognizes an antigen on the progenitor cells CFC-GM, BFU-E, CFC-Eo, and GFC-GEMM, but does not recognize an antigen on mature, human myeloid or lymphoid cells. Anti-My-10 antibody also precipitates a protein from an extract of many human leukemic cells (e.g., KG-1 or KG-1a cells), and is generally found to selectively bind a maximum of about 5% normal, human marrow cells and a maximum of about 1% normal, human peripheral blood cells.

Monoclonal anti-stem cell antibodies can be produced readily by one skilled in the art. The general methodology for making monoclonal antibodies by hybridomas is now well known to the art. See, e.g., M. Schreier et al., *Hybridoma Techniques* (Cold Spring Harbor Laboratory 1980); Hammerling et al., *Monoclonal Antibodies and T-Cell Hybridomas* (Elsevier Biomedical Press 1981); Kennett et al., *Monoclonal Antibodies* (Plenum Press 1980). Immortal, antibody-secreting cell lines can also be produced by techniques other than fusion, such as direct transformation of B-lymphocytes with oncogenic DNA or EBV. Several antigen sources can be used, if desired, to challenge the normal B-lymphocyte population that is later converted to an immortal cell line.

For example, the KG-1a or KG-1 cell lines (preferably the KG-1a cell line) can be used as an immunogen to challenge the mammal (e.g., mouse, rat, hamster, etc.) used as a source for normal B-lymphocytes. The antigen-stimulated B-lymphocytes are then harvested and fused to an immortal cell line or transformed into an immortal cell line by any appropriate technique. A preferred hybridoma producing a monoclonal anti-My-10 antibody is produced by challenging a mouse with the KG-1a cell line and fusing the recovered B-lymphocytes with an immortal mouse plasmacytoma cell. Antibody-producing immortal cells can be screened for anti-stem cell antibody production by selecting clones that are strongly reactive with the KG-1a or KG-1 cells, but not reactive with granulocytes from a panel of human donors. Antibodies produced by clones which show those properties can then be screened for the additional properties of anti-stem cell antibodies.

A mouse hybridoma producing monoclonal anti-My-10 antibody was deposited with the American Type Culture Collection (ATCC), 12301 Parklawn Drive, Rockville, Md. 20852, on Jan. 23, 1984, and assigned ATCC Accession No. HB-8483. The present invention encompasses in a preferred embodiment any monoclonal antibody that recognizes the My-10 antigen, i.e., the antigen recognized by antibody from the hybridoma ATCC HB-8483. In another preferred embodiment, the present invention contemplates monoclonal antibodies that correspond to the monoclonal antibody produced by ATCC HB-8483 and, in a particularly preferred embodiment, the ATCC HB-8483 antibody. One antibody corresponds to another antibody if they both recognize the same or overlapping antigen binding sites as demonstrated by, for example, a binding inhibition assay.

An alternative to the above method of producing monoclonal anti-stem cell antibodies employs the My-10 antigen directly as an immunogen. The monoclonal antibody produced by hybridoma ATCC HB-8483 can be readily employed to precipitate the My-10 antigen. For example, My-10 antigen can be immunoprecipitated from cell extracts of the KG-1a or KG-1 cell lines, or since My-10 is expressed by many other acute leukemic cells, the antigen can be obtained from cell extracts from these sources as well. The precipitated antigen can be used as an immunogen in place of the KG-1a or KG-1 cell line in the above method. By application of any of the above methods, one skilled in the art can readily produce a pannel of monoclonal anti-stem cell and anti-My-10 antibodies.

Another alternative is to use an anti-My-10 antibody in the production of monoclonal antibodies that recognize different antigens on stem cells and the immature marrow cells. The cells isolated from blood and marrow with anti-My-10 antibody can be used as an immunogen, as described above, to produce a panel of monoclonal antibodies against stem cells and immature marrow cells. The production of such anti-stem cell antibodies is greatly facilitated by the use of substantially pure populations of lympho-hematopoietic precursor cells provided by the anti-My-10 antibody as an immunogen. The specificities of such antibodies can be determined readily through routine screening by one skilled in the art. Thus, additional stage-specific, lineage independent antigens (and antibodies to these antigens) can be identified by those of skill in the art.

As indicated above, one application for monoclonal antibodies to stage-specific, lineage independent antigens on stem cells is the isolation of a highly enriched source of stem cells for human bone marrow transplantation. Such sources of stem cells can prevent or attenuate Graft Versus Host Disease. Anti-stem cell monoclonal antibodies (e.g., anti-My-10 antibody) can also be used to isolate stem cells for autologous reinfusion, for example, in the treatment of antigen-negative (e.g., My-10-negative) leukemias or other malignancies.

The present invention contemplates any method employing monoclonal antibodies to separate stem cells from mature lymphocytes in the marrow or blood. Generally, a cell suspension prepared from human tissue containing cells (i.e., marrow or blood cells) is brought into contact with monoclonal antibody (e.g., anti-My-10 antibody) (i) to immature marrow cells that are stage-specific, and not lineage-dependent; (ii) that recognizes an antigen or normal, human stem cells; and (iii) that does not recognize an antigen on normal, mature human myeloid and lymphoid cells. Cells which have been bound by the monoclonal antibody are then separated from unbound cells by any means known to those skilled in the art.

Various methods of separating antibody-bound cells from unbound cells are known. For example, the antibody bound to the cell (or an anti-isotype antibody) can be labeled and then the cells separated by a mechanical cell sorter that detects the presence of the label. Fluorescence-activated cell sorters are well known in the art. In one preferred embodiment, the anti-stem cell antibody is attached to a solid support. Various solid supports are known to those of skill in the art, including, but not limited to agarose beads, polystyrene beads, hollow fiber membranes and plastic petri dishes. Cells that are bound by the antibody can be removed from the cell suspension by simply physically separating the solid support from the cell suspension. Preferred protocols, however, will be described.

Selective cytapheresis can be used to produce a cell suspension from human bone marrow or blood containing pluripotent lymphohematopoeitic stem cells. For example, marrow can be harvested from a donor (the patient in the case of an autologous transplant; a donor in the case of an allogenic transplant) by any appropriate means. The marrow can be processed as desired, depending mainly upon the use intended for the recovered cells. The suspension of marrow cells is allowed to physically contact, for example, a solid phase-linked monoclonal antibody that recognizes an antigen on the desired cells. The solid phase-linking can comprise, for instance, adsorbing the antibodies to a plastic, nitrocellulose or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6MB macrobeads ®. The exact conditions and duration of incubation for the solid phase-linked antibodies with the marrow cell suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound marrow cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petrie dish by vigorous agitation. Alternatively, bound cells can be eluted by enzymatically "nicking" or digesting a enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either cryopreserved in a viable state for later use according to conventional technology or immediately infused intravenously into the transplant recipient.

In a particularly preferred embodiment, stem cells can be recovered directly from blood using essentially the above methodology. For example, blood can be withdrawn directly from the circulatory system of a donor and percolated continuously through a device (e.g., a column) containing the solid phase-linked monoclonal antibody to stem cells and the stem cell-depleted blood can be returned immediately to the donor's circulatory system using, for example, a conventional hemapheresis machine. When a sufficient volume of blood has been processed to allow the desired number of stem cells to bind to the column, the patient is disconnected. Such a method is extremely desirable because it allows rare peripheral blood stem cells to be harvested from a very large volume of blood, sparing the donor the expense and pain of harvesting bone marrow and the associated risks of anesthesia, analgesia, blood transfusion, and infection. The duration of aplasia for the transplant recipient following the marrow transplant can also be shortened since, theoretically, unlimited numbers of blood stem cells could be collected without significant risk to the donor.

The above methods of treating marrow or blood cell suspensions produce a suspension of human cells that contains pluripotent lympho-hematopoietic stem cells, but substantially free of mature lymphoid and myeloid cells. The cell suspension also contains substantially only cells that express the My-10 antigen and can restore the production of lymphoid and hematopoietic cells to a human patient that has lost the ability to produce such cells because of, for example, radiation treatment. By definition, a cell population that can restore the production of hematopoietic and lymphoid cells contains pluripotent lympho-hematopoietic stem cells.

The above cell populations containing human pluripotent lympho-hematopoetic stem cells can be used in theraputic methods such as stem cell transplantation as well as others that are readily apparent to those of skill in the art. For example, such cell populations can be administered directly by I.V. to a patient requiring a bone marrow transplant in an amount sufficient to reconstitute the patient's hematopoietic and immune system. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

The following examples are provided to illustrate specific embodiments of the present invention. The examples are included for illustrative purposes only and are not intended to limit the scope of the present invention.

EXAMPLE I

Development of an Anti-My-10 Monoclonal Antibody

The monoclonal antibody, anti-My-10, was produced by hybridizing SP-2 plasmacytoma cells with splenocytes from a BALB/cJ mouse which had been repeatedly immunized with viable KG-1a cells. Four to twelve week old BALB/cJ female mice were obtained from the Jackson Laboratories (Bar Harbor, Me.), and utilized for development and production of monoclonal antibodies. KG-1a cells were obtained from Dr. D. Golde (UCLA).

Antibody secreting hybridomas were produced by fusion of mouse plasmacytoma cells with splenocytes, using the techniques of Kohler and Milstein, (1975) *Nature* 256: 495, as modified by Fazekas de St. Groth and Scheidegger, (1980) *J. Immunol. Methods* 35:1. A BALB/cJ female mouse was hyperimmunized by intraperitoneal injections (four injections over a four month period) of approximately 10 million washed, viable KG-1a cells in saline; the fourth of these injections was five days prior to fusion. Three and four days prior to fusion, the mouse was boosted intravenously with KG-1a cells. Then, the mouse spleen cells were fused with non-immunoglobulin-producing SP-2/0-AG14 (SP-2) mouse plasmacytoma cells and cultured in HAT medium. Fazekas de St. Groth and Scheidegger, (1980) *J. Immunol. Methods* 35:1. Hybridomas were assayed, and the anti-My-10-producing clone was selected for binding to KG-1a cells, but not to human peripheral blood granulocytes. The hybridoma cells were subcloned at least twice. Neat spent hybridoma culture supernate was used as the source of antibody, under conditions (determined in preliminary experiments) sufficient to saturate binding sites on KG-1a cells. The insotypes of all hybridoma- and plasmacytoma-derived antibodies used were determined as previously described. Civin and Banquerigo, (1983) *J. Immunol. Methods* 61:1.

By two weeks, macroscopic colonies were observed in all 48 cultures; the culture supernates were tested in indirect immunofluorescence assays on KG-1a cells, as well as on granulocytes from several normal donors. Four of these initial culture supernates were strongly reactive (at least five times background) with KG-1a cells, but did not react with granulocytes from any donor tested. The hybridoma culture producing the anti-My-10 monoclonal antibody was cloned in soft agarose. Civin and Banquerigo, (1983) *J. Immunol. Methods* 61:1. Anti-My-10 was shown to be an IgG 1 (Kappa) antibody, by enzyme-linked immunosorbent assay, Civin and Bangerigo, (1983) *J. Immunol. Methods* 61:1, using isotype-specific antibodies (Zymed Laboratories, Burlingame, Calif.). The thrice-cloned hybridoma producing monoclonal anti-My-10 antibody is available from the American Type Culture Collection under ATCC Accession No. HB-8483.

EXAMPLE II

Expression of My-10 Antigen on Myeloid Cell Lines and Normal Human Blood and Marrow Cells Cell lines were obtained and cultured as previously described. Strauss et al., (1983) *Blood* 61: 1222. In addition, the recently described HEL human erythroleukemia cell line (Martin and Papayannopoulou, (1982) *Science* 212: 1233) was generously provided by Dr. T. Papayannopoulou (Seattle, Wash.), and was cultivated similarly.

Heparinized (20 units/ml) peripheral blood was obtained from normal laboratory volunteers, and cell types were separated by several techniques. Platelets, red blood cells and peripheral blood mononuclear cells (PBMC) were separated as described previously (Civin et al., (1981) *Blood* 57: 842; Strauss et al., (1983) *Blood* 61: 1222) over Histopaque-1077® (Sigma, St. Louis, MO). Since Todd et al., (1981) *J. Immunol.* 126: 1435, had pointed out that monocytes may adsorb platelet fragments during conventional PBMC preparation as above, defibrinated (rather than heparinized) blood samples were used when monocytes were to be evaluated. Lymphocytes or monocytes in a mixed population of PBMC could be separately analyzed for fluorescence by first selecting a "lymphocyte region" or "monocyte region," on the basis of forward and right angle light scatter (Hoffman and Hansen, (1981) *Int. J. Immunopharmac* 3: 249) using flow cytometry (Spectrum III cytofluorograph; Ortho Diagnostics, Raritan, NJ). In other studies, the monocytes/macrophages in PBMC preparations (1 million cells/ml complete growth medium) were labelled by incubation (37° C., 5% CO2, 45 min.) with 100 million/ml latex microspheres (Dow Diagnostics, Indianapolis, IN). After washing, phagocytic mononuclear cells were identified microscopically (at least 3 beads/cell).

To obtain enriched T- and B-lymphocyte populations, PBMC (5 million/ml complete growth medium) were first depleted of monocytes and macrophages by incubation (37° C., 5% CO2, 90 min.) in plastic petri dishes (Falcon, Oxnard, CA.). The nonadherent PBMC were then washed and fractionated using sheep erythrocyte (E)-rosette formation. Jondal et al., (1972) *J. Exp. Med.* 136: 207. To isolate peripheral blood granulocytes, mononuclear cells were first removed by Histopaque-1077® density gradient centrifugation. The cells beneath the interface of the first gradient were washed once, and granulocytes were then separated from red cells by dextran sedimentation. Small numbers of residual red cells did not interfere with later analysis of antibody binding to leukocytes; if large numbers (greater than 25%) of red cells were present, they were lysed osmotically. Crowley et al., (1980) *New Eng. J. Med.* 302: 1163.

Marrow was aspirated from posterior iliac crests into alpha medium (M. A. Bioproducts, Walkersville, MD) containing preservativefree heparin (100 units/ml Panheprin R; Abbott, Chicago, IL). Excess cells obtained from donor marrow harvested for allogeneic marrow transplantation, or marrow cells from normal volunteers were utilized. Diluted marrow samples were centrifuged over Histopaque-1077®. The interface cells were washed, suspended in complete growth medium, and incubated (37° C., 5% CO2) in petri dishes for at least 90 min. to remove plastic-adherent cells. The low density, plastic nonadherent marrow cells were washed at least once again prior to use. Leukemic blast cells were obtained from patient diagnostic marrow samples as previously described. Civin et al., (1981) *Blood* 57: 842.

The antibodies I2 (Nadler et al., (1981) *Prog. Hematol.* XII: 187–225, anti-HLA-DR), cALLa (Ritz et al., (1980) *Nature* 283: 583, anti-common acute lymphoblastic leukemia antigen), Mo2 (Todd et al., (1981) *J. Immunol.* 126: 1435, monocyte-specific), T11 (Kamoun et al., (1981) *J. Exp. Med.* 153: 207; Howard et al., (1981) *J. Immunol.* 126: 2117, anti-sheep red blood cell receptor of T-cells), and B1 (Nadler et al., (1981) *Prog. Hematol.* XII: 182–225, anti-pan B-cell) were generously provided by Dr. L. Nadler (Sidney Farber Cancer Center, Boston, MA) and Dr. K. Kortwright (Coulter Diagnostics, Hialeah, FL). The antileu-1 monoclonal antibody (Engleman et al., (1981) *Proc. Natl. Acad. Jei. USA* 78: 1891) was generously provided by Dr. R. Levy (Stanford, Palo Alto, CA). The MOPC 21 IgG 1 (Kappa) mouse myeloma protein, produced by P3×63. AG8 cell line (American Type Tissue Collection, Rockville, MD) and having no known specificity, was utilized as a negative control antibody (culture supernate). The 28/43/6 monoclonal antibody, which binds to lymphocytes from all donors tested (Strauss et al., (1983) *Blood* 61: 1222), was used as a positive control.

Indirect immunofluorescence assays to measure binding of monoclonal antibodies to cells were performed as previously described. Civin et al., (1981) *Blood* 57: 842; Strauss et al., (1983) *Blood* 61: 1222. Binding was analyzed either by standard phase and fluorescence microscopy and/or by flow microfluorometry.

Large quantities of cell surface My-10 antigen (indirect immunofluorescence assay) were detected by flow microfluorometry and other methods on KG-1a cells. The anti-My-10-labelled KG-1a cell population was even (slightly) more intensely fluorescent than the (positive control) 28/43/6-labelled sample (Table 1). In contrast, when the other cell lines were labelled with anti-My-10, neither the fluorescence histograms nor the derived values were greatly different from the negative control (MOPC 21) profile. (Daudi and K-562 cells were not detectably labelled with the positive control 28/43/6 antibody. This is consistent with the thesis that this antibody detects a framework epitope of the HLA-A,B molecule, since HLA-A,B is not expressed on Daudi or K0562 cells. Strauss et al., (1983) *Blood* 61: 1222). In this experiment, Daudi cells appeared slightly positive for MY-10. However, in other experiments, all of these cell lines (except KG-1a) were clearly negative for anti-My-10-binding. The same conclusions were reached when whole viable cells were tested by enzyme-linked immunoassays (EIA), and when purified anti-My-10 was used rather than tissue culture supernate.

positive marrow cells, there is cellular heterogeneity with regard to My-10 antigen cell surface density, from near background to off-scale at these instrument settings. Mean fluorescence intensity of the anti-My-10-treated marrow cells was 1.2, compared to 0.8 with MOPC 21 and 15.6 with 28/43/6. 2.1% of anti-My-10-treated marrow cells were more fluorescent than the 99.9 percentile cell treated with MOPC 21. FACS II oscilloscope fluorescence vs. light scatter "dot plots" of these marrow cells at two FACS II laser voltage settings were made.

TABLE 1

My-10 Antigen Expression on Human Leukemic Cell Lines: Derived Population Fluorescence*

|  | MOPC 21 (Negative Control) | | Anti-My-10 | | 28/43/6 (Positive Control) | |
| --- | --- | --- | --- | --- | --- | --- |
|  | Mean Fluorescence Intensity** | Percent Bright Cells*** | Mean Fluorescence Intensity | Percent Bright Cells | Mean Fluorescence Intensity | Percent Bright Cells |
| KG-1a | 1.2 | [10%] | 10.0 | 92% | 9.5 | 81% |
| U-937 | 1.5 | [10] | 1.8 | 17 | 17.1 | 97 |
| Daudi | 1.0 | [10] | 1.8 | 22 | 1.1 | 13 |
| ML-1 | 0.8 | [10] | 1.0 | 15 | 4.0 | 91 |
| MOLT-3 | 1.0 | [10] | 1.9 | 19 | 5.0 | 77 |
| HEL | 1.9 | [10] | 3.3 | 21 | 12.2 | 78 |
| HL-60 | 2.9 | [10] | 1.6 | 2 | 29.0 | 86 |
| K-562 | 3.3 | [10] | 2.3 | 9 | 1.9 | 2 |

*Values derived from histograms.
**Normalized mean population intensity of fluorescence. See Durand, (1982) Cytometry 2: 192.
***Percent of cells brighter than 90th percentile fluorescence with negative control (MOPC21) monoclonal antibody.

TABLE 2

My-10 Antigen Expression on Blood and KG-1 Cells: Derived Population Fluorescence*

|  | MOPC 21 | | Anti-MY-10 | | 28/43/6 | |
| --- | --- | --- | --- | --- | --- | --- |
|  | Mean Fluorescence Intensity | Percent Bright Cells | Mean Fluorescence Intensity | Percent Bright Cells | Mean Fluorescence Intensity | Percent Bright Cells |
| Lymphocytes | 0.3 | [10%] | 0.3 | 8% | ND** | ND |
| Granulocytes | 1.0 | [10] | 0.9 | 6 | ND | ND |
| Monocytes | 1.4 | [10] | 1.4 | 13 | 17.5 | 86% |
| KG-1 | 0.8 | [10] | 2.0 | 13 | 5.4 | 87 |

*Values derived from histograms and calculated as in Table 1.
**Not done.

Table 2 shows FACS fluorescence data of isolated peripheral blood granulocytes, plastic-adherent monocytes (86% monocytes by Wright-Giemsa stain), and nonadherent "lymphocytes" (66% lymphocytes by Wright-Giemsa stain) after reaction with anti-My-10. No specific fluorescence was detected. In several additional immunofluorescence and EIA assays, anti-My-10 did not label peripheral blood granulocytes, mononuclear cells (including E-rosette-positive and E-rosette-negative cells, and latex bead-labelled phagocytic cells, analyzed individually), red cells, or platelets from any of 9 noral human blood donors.

Low-density, plastic-nonadherent, marrow cells from normal human donors were analyzed for cell surface expression of My-10 antigen by indirect immunofluorescence using visual microscopic detection. A small, but definite (1.3% mean) subpopulation of marrow cell was fluorescent over MOPC 21 background in eight experiments. A small subpopulation of My-10-positive marrow leukocytes was also identified by flow cytometry. KG-1a cells, tested in the same experiment, are shown for comparison. In both the KG-1a cells and the My-10-

EXAMPLE III

Morphologic and Cytochemical Phenotype of My-10-Panned Marrow Cells

The technique of Engleman et al., *Proc. Natl. Acad. Sci. USA* 78: 1891, was utilized as previously described. Strauss et al., (1983) Blood 61: 1222. Briefly, to non-tissue culture-treated plastic petri dishes (Lab-Tek, Naperville, Il; 60 mm) was added 5 ml of sterile Tris buffer (0.1M, pH 9.2) containing 20 ug/ml affinity-purified goat anti-mouse IgG antibody (Kirkegaard and Perry). After 45 minutes (22° C.), the dishes were rinsed three times with Hank's balanced salt solution (HBSS), then once with HBSS containing 0.2% Bovine serum albumin (BSA), and stored (4° C.) in the latter medium. Immediately prior to use, dishes were washed with HBSS containing 0.2% BSA.

Plastic-nonadherent, low density marrow leukocytes were adjusted to 5 million/ml in HBSS containing 0.2% BSA and incubated (30 min., 22° C.) with an equal volume of spent hybridoma supernate (conditions of antibody excess, as determined in preliminary experiments). Cells were then washed twice in cold HBSS containing 0.2% BSA. Ten million cells in 2 ml of the same cold medium were placed in a goat-anti-mouse Ig-coated petri dish at 4° C. The dish was rocked gently after one hour, and after two hours, the unbound cells were harvested by rocking and gently pipetting with three 2 ml volumes. The bound cells were released by 3 rinses with vigorous pipetting.

Only 1.7–2.2% of the normal human low density, plastic nonadherent, bone marrow cells bound to the My-10 panning plates in these four experiments. Cell fractions were then cytocentrifuged and stained for morphology (Table 3). The small My-10-positive marrow cell fraction contained many undifferentiated blast cells (Table 3). Small numbers of progranulocytes, more mature granulocytic cells, and lymphoid cells were also observed in this cell fraction. These results were confirmed by analysis of double esterase cytochemical stains of the cell fractions (Table 4) which suggested the presence of both monoblasts (nonspecific esterase-positive) and myeloblasts (NASD chloroacetate esterase-positive).

Smeared or cytocentrifuged preparations of whole or separated marrow cells or colonies were stained either with Wright-Giemsa stain, or with a double-esterase (alpha-naphthyl acetate and naphthol AS-D chloroacetate esterases) cytochemical stain and Mayer's Hematoxylin counterstain for differential counting, or with other cytochemical stains (Yam et al., (1971) *Am. J. Clin. Path.* 55: 283).

TABLE 3

Differential Blood Counts* of
My-10-Antigen-Positive vs. Negative Marrow Cells

| Marrow Cells: | Unseparated | | My-10-Neg. | | My-10-Pos. | |
|---|---|---|---|---|---|---|
| | Exp 1*** | Exp 2 | Exp 1 | Exp 1 | Exp 1 | Exp 2 |
| Blast cells | 2 | 2 | 7 | 6 | 74 | 62 |
| Promyelocytes | 4 | 4 | 7 | 3 | 5 | 7 |
| Myelo-Neutro** | 53 | 54 | 40 | 44 | 6 | 2 |
| Basophils/Eosinophils | 1 | 0 | 1 | 1 | 1 | 1 |
| Monocytes | 9 | 3 | 4 | 1 | 4 | 0 |
| Lymphocytes | 25 | 27 | 34 | 43 | 7 | 26 |
| Plasmacytes | 1 | 1 | 0 | 0 | 1 | 1 |
| Erythroblasts | 3 | 11 | 6 | 3 | 1 | 0 |

| Marrow Cells: | Unseparated | | My-10-Neg. | | My-10-Pos. | |
|---|---|---|---|---|---|---|
| | Exp 3 | Exp 4 | Exp 3 | Exp 4 | Exp 3 | Exp 4 |
| Blast cells | 18 | 10 | 1 | 7 | 23 | 65 |
| Promyelocytes | 6 | 24 | 10 | 15 | 16 | 14 |
| Myelocytes | 4 | 17 | 11 | 4 | 4 | 0 |
| Metamyelocytes | 23 | 2 | 5 | 2 | 12 | 0 |
| Band forms | 1 | 0 | 12 | 0 | 16 | 0 |
| Segmented neutrophils | 36 | 1 | 0 | 0 | 3 | 0 |
| Basophils | 0 | 2 | 1 | 0 | 2 | 0 |
| Eosinophils | 0 | 0 | 3 | 0 | 2 | 0 |
| Monocytes | 0 | 3 | 0 | 2 | 1 | 2 |
| Lymphocytes | 3 | 25 | 29 | 42 | 22 | 16 |
| Plasmacytes | 0 | 1 | 0 | 1 | 0 | 1 |
| Erythroblasts: | | | | | | |
| Orthochromatophilic | 7 | 12 | 26 | 20 | 0 | 0 |
| Basophilic | 1 | 3 | 2 | 6 | 0 | 0 |
| Polychromatophilic | 2 | 0 | 0 | 1 | 0 | 1 |
| Proerythroblasts | 0 | 2 | 1 | 0 | 0 | 0 |

*Percent of at least 200 Wright's-stained cells counted (rounded).
**Myelocytes, metamyelocytes, band forms, plus segmented neutrophils.
***Exp = Experiment.

TABLE 4

Cytoplasmic Esterase Content of
My-10-Antigen-Positive vs. Negative Marrow Cells*

| Marrow Cells: | Unseparated | | My-10-Neg. | | My-10-Pos. | |
|---|---|---|---|---|---|---|
| | Exp. 3 | Exp. 4 | Exp. 3 | Exp. 4 | Exp. 3 | Exp. 4 |
| Naphthol AS-D Chloroacetate esterase-positive** | 66 | 34 | 40 | 16 | 36 | 2 |
| Alpha naphthyl acetate esterase-positive | | | | | | |
| Diffusely Stained | 1 | 6 | 1 | 0 | 5 | 0 |
| Focally Stained | 0 | 0 | 7 | 1 | 2 | 0 |
| Unstained | 33 | 62 | 52 | 83 | 55 | 98 |

*Percent of 200 cells counted (rounded). Data for experiments 3 and 4 are from the experiments designated by the same numbers in Table 3.
**"Nonspecific esterase."

EXAMPLE IV

Anti-My-10-Immune Rosetting Human Marrow Cells

Previously described procedures (Goding, (1976) *J. Immunol. Methods* 10: 61; Parish and McKenzie, (1978) *J. Immunol. Methods* 20: 173) were modified as described below. Human O-negative red cells were purified from heparinized fresh whole blood by centrifugation (300×g 30 min., 22° C.) over Mono-Poly-Resolving Medium (Flow Laboratories, McLean, VA). The leukocyte-free, erythroid cell pellet was washed five times in sterile 0.9% NaCl (4° C., 300×g, 10 min.) and stored 16 hours as a 10% suspension in isotonic saline (4° C.). Affinity-purified goat anti-mouse IgG (Kirkegaard and Perry), and protein A-sepharose column (Pharmacia, Piscataway, NJ) -purified (Ey et al., (1978) *Immunochem* 15: 429) monoclonal antibody (anti-My-10, MOPC 21, or 28/43/6) in isotonic saline were centrifuged (15,600×g, 30 min., 4° C.) to remove macroaggregates immediately prior to use. Immune red cells were prepared by the dropwise addition of 0.5 ml 0.01% chromic chloride to a (4° C.) suspension containing 350 ul isotonic saline, 50 ul freshly washed packed red cells, and 50 ul antibody (1 mg/ml). After five min. (22° C.), an equal volume of phosphate-buffered saline (PBS) containing 0.1% sodium azide was added to stop the reaction. The immune red cells were washed by centrifugation, transferred to a fresh test tube, then washed again and resuspended to a 10% suspension in PBS containing 0.1% sodium azide and 10% fetal bovine serum (FBS). All manipulations were under aseptic conditions. The immune red cells were kept at 4° C. until use later that day.

In the direct immune rosetting procedure, one million low density, plastic-nonadherent marrow cells in 100 ul PBS containing 0.1% sodium azide and 10% FBS were mixed with 50 ul immune red cell suspension. After gentle centrifugation (200×g, 5 min., 4° C.), cells were mixed gently, then kept at 4° C. for one hour. Next, 3 ml of HBSS containing 0.2% bovine serum albumin was added. Aliquots were cytocentrifuged and stained for morphological analysis. To the residual volume, one drop of 1% gentian violet was added, and wet mounts were prepared and counted.

For the indirect immune rosetting procedure, cells were first incubated with centrifuged McAb (60 min., 4° C.), washed twice, then rosetted with goat-anti-mouse IgG-coated red cells as in the procedure for direct rosettes.

1.5–3% of nucleated marrow cells were My-10-positive by these assays. Morphologic analysis of cytocentrifuged rosette preparations indicated that few mature cells formed rosettes and that the predominant My-10-positive cells were blast cells (Table 5), although not all blast cells were My-10-positive (by either panning or immune rosetting).

TABLE 5

Anti-My-10 Immune Rosetting-Human Marrow Cells: Differential Nucleated Cell Counts*

| | Anti-My-10-Rosetting Marrow Cells** | | |
|---|---|---|---|
| | Direct Assay | Indirect Assay | Whole Marrow |
| Blast Cells | 48% | 63% | 10% |
| Promyelocytes | 11 | 8 | 10 |
| Myelocytes | 0 | 0 | 13 |
| Metamyelocytes | 0 | 1 | 16 |
| Band forms and segmented neutrophils | 11 | 8 | 18 |
| Monocytes | 0 | 0 | 15 |
| Lymphocytes | 8 | 1 | 10 |
| Orthochromatophilic normoblasts | 2 | 2 | 6 |
| Polychromatophilic normoblasts | 0 | 0 | 3 |
| Unidentifiable*** | 20 | 17 | 0 |

*Based upon 200 cell counts (rounded). Whole marrow was taken as the first 200 nucleated cells seen on the indirect anti-My-10 test slide, whether rosetted or not.
**In wet mounts from this experiment, 1.5% of marrow cells formed direct anti-My-10 rosettes, and 3.0% formed indirect anti-My-10 rosettes. Comparison results using MOPC 21 control rosettes were 0% (direct and indirect), and using 28/43/6 rosettes were 100% (direct and indirect).
***Morphology obscured by rosetted erythrocytes.

EXAMPLE V

Expression of My-10 by Human Myeloid Colony-Forming Cells for Granulocytes and Monocytes (CFC-GM)

Normal marrow cell fractions obtained as above were assayed for CFC-GM in semisolid agar cultures.

Day 12–14 CFC-GM were assayed in triplicate in semi-solid agar with 5% placenta-conditioned medium (Pike and Robison, (1970) *J. Cell. Physiol.* 76: 77; Burgess et al., (1977) *Blood* 49: 573) exactly as described previously (Strauss et al., (1983) *Blood* 61: 1222). Day 14 multilineage colonies (Fauser and Messner, (1979) *Blood* 53: 1023; Nakahata et al., (1982) *Blood* 59: 857; Iscove, et al., (1974) *J. Cell. Physiol.* 83: 309) were assayed in quadruplicate in medium containing 0.96% methylcellulose, 5% placenta-conditioned medium, and 1 unit/ml erythropoietin (Connaught, Torronto, ONT). Colony number was a linear function of total cells plated. It should be noted that, in most experiments, cells were plated at several dilutions to obtain countable plates (20–200 colonies). This was particularly important with My-10-positive cell fractions, which were enriched in colony-forming cells. In addition, mixed lineage colonies were not scored on plates with more than 100 total colonies per plate, to avoid scoring superimposed colonies as products of a single colony-forming cell.

Colonies were counted in situ using a dissecting microscope (50–80×) or inverted phase microscope (200×), and gross colony and cellular morphology was recorded. Representative colonies were plucked using a Pasteur pipette. Stained cytocentrifuge preparations were analyzed for confirmation of cell type(s) within the colonies.

Less than 10% of the CFC-GM were detected in the My-10-negative cell fraction, and the My-10-positive cell fraction was several-fold enriched for CFC-GM, compared to unfractionated marrow or control IgG1 (MOPC 21)-bound marrow cells (Table 6). However, only approximately 40% of the CFC-GM of the initial marrow sample were recovered in the My-10-positive cell population. This might be explained by mechanical injury to the My-10-positive cells or by partition of an accessory cell type Sharkis et al., (1981) In Gershwin and Merchant (eds), *Immunologic Defects in Laboratory Animals* (Plenum, NY) 1:79; Strauss et al., (1983) *Blood*, in press).

Marrow cell fractions obtained by My-10-panning were also cultured in medium containing methylcellulose. As in agar cultures, CFC-GM were almost totally depleted from the My-10-negative fraction (Tables 7,8). In the experiment shown in Table 7, the My-10-positive fraction was approximately 30-fold enriched in CFC-GM and contained 90% of the initial CFC-GM (the full recovery of CFC-GM in this experiment contrasted with yields of CFC-GM in agar cultures described above.) CFC-GM colony subtypes (granulocyte, monocyte vs. granulocyte/monocytes [data not shown]; small vs. large colonies) were found in similar proportions in the My-10-positive and control cell populations.

Pure erythroid colonies were enumerated at Day 14 in the same panned marrow cell fractions (methylcellulose-containing cultures, Table 7, 8). Pure erythroid colonies were several-fold enriched in the My-10-positive fraction, but some erythroid colonies were also present in the My-10-negative cell populations. It was noted that all of the large (more than 200 cells) erythroid colonies with the microscopic characteristics of BFU-E (multiple hemoglobinized clusters of cells forming a large colony) were My-10-positive. Though small (less than 200 cell) erythroid colonies (enumerated on day 14, but with the morphology of CFU-E in that they were composed of only a single cluster of hemoglobinized cells) were enriched in the My-10-bound fraction, substantial numbers of small erythroid colonies were My-10-bound.

Smaller numbers of pure eosinophilic colonies were observed in these methylcellulose-containing marrow cultures. The pure eosinophilic colonies (CFC-Eo) were depleted in the My-10-negative fraction and enriched in the My-10-positive fraction (Table 7, 8). Over 80% of CFC-Eo were My-10-positive by this methodology. Even smaller numbers of mixed eosinophilic-erythroid colonies (CFC-EEo) were observed, all in the My-10-positive cell population (Table 7, 8).

TABLE 6

CFC-GM (agar cultures) in My-10-Panned Normal Human Marrow Cells

| | MOPC 21 | | My-10 | |
|---|---|---|---|---|
| | Unbound | Bound | Unbound | Bound |
| A. Single Experiment: | | | | |
| Recovered Viable Cells* | 84% | 1% | 77% | 3% |
| CFC-GM per $10^5$ Cells** | 63(±5)**** | ND † | 2(±1) | 883(±6) |
| Recovered CFC-GM*** | 5290 | ND | 192 | 2650 |
| B. Averaged Data: (9 experiments) | | | | |
| Recovered Viable Cells | 83(±2)% | 3(±1)% | 81(±1)% | 6(±1)% |
| CFC-GM Enrich- | [1] | 0† ††† | 0.08(±0.02) | 8(±2) |

TABLE 6-continued

CFC-GM (agar cultures) in My-10-Panned Normal Human Marrow Cells

|  | MOPC 21 | | My-10 | |
| --- | --- | --- | --- | --- |
|  | Unbound | Bound | Unbound | Bound |
| ment †††<br>CFC-GM<br>Recovery | [100%] | 0% | 9(±3)% | 42(±5)% |

*Values represent (100%) × (viable cell number in fraction)/(initial cell number treated with McAb).
**Arithmetic mean (± standard deviation) of at least triplicate determinations (rounded).
***Product of (CFC-GM/$10^5$) cells) × (number of viable cells in fraction).
****Similar results obtained with unfractioned marrow cells.
† Not done.
† † (CFC-GM per $10^5$ cells in given cell fraction)/(CFC-GM per $10^5$ cells in MOPC-21-unbound fraction for that experiment). Mean ± 1 standard error of the mean (SEM).
† † † (100%) × (Recovered CFC-GM in given fraction)/(Recovered CFC-GM in MOPC-21-unbound fraction for that experiment). Mean ± 1 SEM.
† † † † The MOPC-21-bound fraction was large enough to permit plating for CFC-GM on only 2 of these 9 experiments. In both of these experiments and in 6 additional experiments, no CFC-GM colonies grew on the plates.

TABLE 7

Colonies in Methylcellulose Culture After Panning (single experiment)

|  | MOPC 21 | | My-10 | |
| --- | --- | --- | --- | --- |
|  | Unbound | Bound | Unbound | Bound |
| Recovered Viable Cells*: | 84% | 1% | 77% | 3% |
| Large† CFC-GM: | | | | |
| Per $10^5$ Cells** | 57(±6) | ND †† | 1(±1) | 1600(±180) |
| Recovery*** | 4790 | ND | 77 | 4800 |
| Small† CFC-GM: | | | | |
| Per $10^5$ Cells | 106(±17) | ND | 5(±2) | 3650(±400) |
| Recovery | 8900 | ND | 385 | 10950 |
| Large † Erythroid: | | | | |
| Per $10^5$ Cells | 58(±2) | ND | 0(±0) | 1450(±200) |
| Recovery | 4870 | ND | 0 | 4350 |
| Small † Erythroid: | | | | |
| Per $10^5$ Cells | 142(±2) | ND | 94(±12) | 1970(±490) |
| Recovery | 11930 | ND | 7240 | 5850 |
| CFC-EEo †††: | | | | |
| Per $10^5$ Cells | 2(±1) | ND | 0(±0) | 50(±0) |
| Recovery | 168 | ND | 0 | 150 |
| CFC-Eo †††: | | | | |
| Per $10^5$ Cells | 14(±2) | ND | 3(±1) | 380(±150) |
| Recovery | 1090 | ND | 231 | 1200 |

*, , *Same as Table 6.
† Large colonies contained at least 200 cells, small colonies less than 200 cells.
† † Not done.
† † † CFC-Eo = pure eosinophil colonies. CFC-EEo = mixed colonies of the CFC-GEMM-type containing erythrocytes and eosinophils.

TABLE 8

Percent of Colonies in My-10-Bound Marrow Cell Panning Experiments*

|  | Percent Recovered in My-10 Bound Fraction |
| --- | --- |
| Viable Cells | 4(±1)% |
| Large CFC-GM | 95(±2) |
| Small CFC-GM | 84(±8) |
| Large Erythroid | 78(±10) |
| Small CFC-GM | 46(±14) |
| CFC-EEo | 98(±2) |
| CFC-Eo | 86(±6) |

*Arithmetic means (rounded ± 1 SEM) in 4 experiments plated in methylcellulose cultures. Definitions of colony types, etc., as in Table 7.

EXAMPLE VI

FACS II Sorting of My-10-Treated Marrow Cells

Under aseptic conditions, normal low density, nonadherent marrow cells were incubated with centrifuged anti-My-10, washed, then reacted with centrifuged, fluorescein-conjugated, anti-mouse IgG (as above for analytical indirect immunofluorescence). After washing, the cells were analyzed and stored on the basis of fluorescence intensity (FACS II). "My-10-bright" cells were defined as more than 50 channels fluorescence intensity (1.93% of total My-10-treated cells; in contrast, 0.05% of the MOPC-21-treated cells were brighter than 50 channel units). The FACS II was adjusted to deflect anti-My-10-treated cells with fluorescence intensity less than 30 channels into the "My-10-dull" fraction (97.14% of total sorted cells). A "window" of cells between 30–50 channels fluorescence intensity (0.93% of total My-10-treated cells) was discarded to minimize overlap. The My-10-bright fraction consisted almost entirely of morphologically-defined blast cells (Table 9) Cytochemical assays suggested that the FACS-separated My-10-positive blast cells were heterogeneous, containing at least monoblasts and myeloblasts (confirming cytochemical studies on panned My-10-positive cells).

The My-10-positive fraction contained essentially all of the colony-forming cells, and was more than 50-fold enriched for these progenitor cell types (Table 10). 18% of the My- 10-positive cells formed colonies detectable in this culture system. These FACS results are in agreement with the results using the panning methodology, except that FACS apparently yielded a population of My-10-positive cells that was more enriched in primitive and clonogenic cells.

TABLE 9

Cytochemical Analysis of FACS-Separated My-10-Antigen-Positive Primitive Cells*

| Cytochemical Stain | Percent Primitive Cells Cytochemically Positive** |
| --- | --- |
| Peroxidase | 14% |
| Sudan Black | 10 |
| Periodic Acid Schiff | 16 |
| NASD Chloroacetate Esterase | 8 |
| Nonspecific Esterase: Diffusely Stained | 28*** |
| Focally Stained | 1*** |

*3% of the FACS-Separated My-10-antigen-positive cells were matured neutrophils (metamyelocytes, band forms, segmented neutrophils), 6% were mature monocytes, and 1% were mature lymphocytes. These mature cells were nc. scored in this analysis of the "primitive blast" cells (84%, all morphologically immature with a fine, open chromatin pattern) and promyelocytes (6%).
**200 cells counted; each cytochemical test was done on a separate slide, except for the esterases which were done on the same slide.
***Values were zero with NaF added (NaF inhibits nonspecific esterase of monocytes).

TABLE 10

Colonies in Methylcellulose Culture After FACS Experiment

|  | Unsorted* | My-10-Dull | My-10-Bright |
| --- | --- | --- | --- |
| Recovered Viable Cells: | [100%] | 97% | 2% |
| Colonies per $10^5$ Cells**: | | | |
| Large CFC-GM | 50(±21) | 0(±0) | 4150(±680) |
| Small CFC-GM | 147(±41) | 2(±0) | 7750(±1980) |
| Large Erythroid | 9(±1) | 0(±0) | 1800(±690) |
| Small Erythroid | 52(±6) | 4(±1) | 3400(±910) |

TABLE 10-continued

Colonies in Methylcellulose Culture After FACS Experiment

|  | Unsorted* | My-10-Dull | My-10-Bright |
|---|---|---|---|
| Eosinophil-containing | 11(±7) | 0(±0) | 550(±380) |

*Cells were anti-My-10-treated and passed through FACS laser, but not sorted.
**Definitions of methylcellulose culture CFC-GM and erythroid colonies as described in text and previous Tables. Eosinophil-containing colonies include CFC-Eo and CFC-EEo. Low erythroid colony growth was observed in this experiment.

EXAMPLE VII

Immunoprecipitation of a Radiolabelled KG-1a Antigen by Anti-My-10

Vectorial labelling of the plasma membrane of intact cells with 125 I-iodide, followed by immunoprecipitation with SA-bound monoclonal antibody, SDS-PAGE analysis, and visulization of antigen by autoradiography, was utilized to identify the KG-1a membrane protein detected by anti-My-10. Under reducing as well as non-reducing conditions, My-10 antigen had an Mr of approximately 115 kD, indicating the absence of disulfide-linked oligomers.

KG-1a cells were radiolabelled vectorially within 125 I-iodide using the method of Hubbard and Cohn ((1972) J. Cell Biol. 55: 390). Briefly, 20 million cells in exponential growth were washed four times in 10 mM Hepes—0.15M NaCl buffer, pH 7.4 (Buffer A). The cell pellet was resuspended in one ml of Buffer A containing 0.05M glucose, 40 ul of (100 IU/ml) lactoperoxidase (Calbiochem-Behring, San Diego, CA), and 2.5 ul of freshly prepared (1 mg/ml) glucose oxidase (Millipore Corp., Freehold, NJ). 0.5-1 mCi of 125 I-iodide (New England Nuclear, Boston, MA) was added, and the cell suspension was incubated at 22° C. for 20 minutes with gentle agitation. Then 10 ml of Buffer A containing 4 mM KI and 0.1% glucose was added to stop the reaction. After four washes with Buffer A, the cell pellet was resuspended in 500 ul of disruption buffer (10 mM EDTA, and 50 ug/ml Leupeptin [Sigma]) for 20 minutes on ice with periodic vortexing. The cell extract was then centrifuged (10 minutes, 15,600×g, 4° C.), and the supernate used for immunoprecipitation.

Immunoprecipitation was performed essentially as described by Lampson, in Monoclonal Antibodies 395-397 (Kennett, et al. 1980). For each monoclonal antibody to be tested, 300 ul of 10% fixed, whole, protein A-bearing Cowan strain Staphylococci (SA; Calbiochem-Behring) was washed three times by centrifugation (15,600×g, 5 min., 4° C.) in Lampson wash buffer (WB) (0.1M phosphate-buffer saline, pH 8.6, containing 0.1% BSA, 0.02% NaN3, 0.5% NP40, 0.1% SDS). The SA pellet was then resuspended to the initial volume with goat anti-mouse IgG serum (Kierkegaard and Perry, Gaithersburg, MD) and incubated 12-18 hrs. at 4° C. The SA-IgG complex was washed seven times in WB and suspended with monoclonal antibody (hybridoma culture supernate) to 10% (v/v). After 40 minutes incubation (22° C.), the SA-IgG-monoclonal antibody complex was washed three times in WB and resuspended to the initial volume in WB. To this complex, 80-120 ul of cell extract was added, followed by incubation at 4° C. for 12-18 hours. the SA-IgG-monoclonal antibody complex was then washed three times in WB and resuspended in 50 ul of WB plus 25 ul of Laemmli ((1970) Nature 227: 680) sample buffer (0.0625M Tris HCl, pH 6.8, containing 12.5% glycerol, 1.25% 2-mercaptoethanol, 5% SDS and 1 mM EDTA), boiled for two minutes, centrifuged (15,600×g, 5 min.), and the supernate harvested for analysis by SDS-polyacrylamide gel electrophoresis.

The samples were analyzed on 10% SDS-polyacrylamide gels under reducing conditions according to the method of Laemmli ((1970) Nature 227: 680). After electrophoresis, the gel was stained with Coomassie brilliant blue, destained, dried onto filter paper and exposed to X-ray AR film (Kodak, Rochester, NY) at −70° C.

EXAMPLE VIII

Reactivity of Anti-My-10 with Diagnostic Specimens from Patients with Acute Leukemia Initial diagnostic marrow specimens from Johns Hopkins Oncology Center patients found to have leukemia, with at least 80% marrow blast cells, were tested with these antibodies by indirect immunofluorescence. Specimens which contained at least 20% fluorescent cells (over background) were counted as "positive" for that antigen (Strauss et al., (1983) Blood, in press). The My-10 antigen was expressed on blast cells from approximately 30% of the acute leukemia specimens, both lymphocytic and nonlymphocytic, but on none of the few chronic leukemia specimens tested, including two specimens of chronic myelogenous leukemia (CML) in "myeloid" blast crisis or other specimens tested (Table 11).

TABLE 11

Reactiviy of Patients' Marrow* Leukemic Blast Cells With Anti-My-10

| Disease** |  | Percent Positive Specimens*** |
|---|---|---|
| Acute Nonlymphocytic Leukemia |  | 28% (18/65) |
| Acute Lymphocytic Leukemia |  | 32% (10/31) |
| cALLa-positive | (8/23) |  |
| HLA-DR-positive, cALLa-negative | (2/3) |  |
| T-cell (leu-1 or T11-positive) | (0/5) |  |
| Chronic Lymphocytic Leukemia |  | 0% (0/10) |
| Chronic Myelogenous Leukemia |  | 0% (0/3) |
| Myeloblastic crisis | (0/1) |  |
| Basophilic blast crisis | (0/1) |  |
| Untreated chronic phase | (0/1) |  |
| Mycosis fungoides** |  | 0% (0/1) |
| Lymphoma |  |  |
| Non-T, non-B | (0/1) | 0% (0/2) |
| B-cell | (0/1) |  |
| Undifferentiated carcinoma (marrow involvement) |  | 0% (0/1) |

*Peripheral blood (at least 80% leukemic mononuclear cells) was studied instead of bone marrow in 9 chronic lymphocytic and 3 acute lymphocytic leukemia specimens as well as in the 1 mycosis fungoides specimen. Ascites cells or mechanically dissociated cells from lymphomatous nodes were studied in the 2 patients with lymphoma.
**Diagnosis defined by clinical features, blast cytomorphology and cytochemistry, and immunologic markers. See Nadler et al., Diagnosis and Treatment of Human Leukemias and Lymphomas Utilizing Monoclonal Antibodies, pp. 184-225 (E. Brown 1981).
***Values represent percent of specimens with at least 20% (above MOPC 21 background) antibody-labelled cells (number positive specimens/number treated).

Since variations will be apparent to those skilled in the art, it is intended that this invention be limited only by the scope of the appended claims.

I claim:

1. A method of transplanting stem cells comprising:
(a) providing a suspension of human cells comprising pluripotent lympho-hematopoietic stem cells substantially free of mature lymphoid and myeloid cells, having the ability to restore the production of lymphoid and hematopoietic cells in a patient where such production is lacking; and (b) administering said cell suspension to a human patient in an amount effective to effect such restoration.

2. The method of transplanting stem cells, as recited in claim 1, wherein said cell suspension further comprises colony-forming cells for granulocytes/monocytes (CFC-GM), colony-forming cells for erythrocytes (BFU-E), colony-forming cells for eosinophils (CFC-Eo), multipotent colony-forming cells (CFC-GEMM), and immature lymphoid precursor cells.

3. A method of transplanting stem cells, comprising:
(a) providing a suspension of human stem cells comprising pluripotent lympho-hematopoietic stem cells substantially free of mature lymphoid and myeloid cells, said suspension having the ability to restore the production of lymphoid and hematopoietic cells to a human lacking said production; and (b) administering said cell suspension to a human patient in an effective amount;

wherein said suspension of human cells is substantially free of cells without a cell-surface antigen recognized by the monoclonal antibody produced by the hybridoma deposited under ATCC Accession No. HB-8483.

4. A method of transplanting stem cells, comprising:
(a) providing a suspension of human cells from marrow or blood comprising cells having a cell-surface antigen recognized by the antibody produced by the hybridoma deposited under ATCC Accession No. HB-8483 and substantially free of cells that do not have a cell-surface antigen recognized by said antibody, said suspension having the ability to restore the production of lymphoid and hematopoietic cells to a human lacking said production;

(b) administering said cell suspension to a human patient in an effective amount.

* * * * *

REEXAMINATION CERTIFICATE (2657th)

United States Patent [19]

Civin

[11] B1 5,130,144
[45] Certificate Issued Aug. 15, 1995

[54] HUMAN STEM CELLS AND MONOCLONAL ANTIBODIES

[75] Inventor: Curt I. Civin, Baltimore, Md.

[73] Assignee: The Johns Hopkins University, Baltimore, Md.

Reexamination Request:
No. 90/003,402, Apr. 15, 1994

Reexamination Certificate for:
Patent No.: 5,130,144
Issued: Jul. 14, 1992
Appl. No.: 673,721
Filed: Mar. 22, 1991

Related U.S. Application Data

[62] Division of Ser. No. 580,337, Sep. 7, 1990, which is a division of Ser. No. 55,942, Jun. 1, 1987, Pat. No. 4,965,204, which is a division of Ser. No. 670,740, Feb. 6, 1984, Pat. No. 4,714,680.

[51] Int. Cl.$^6$ .................. A61K 35/28; C12N 5/08
[52] U.S. Cl. ................................ 424/577; 435/240.2
[58] Field of Search ............... 424/93.1, 93.3, 93.7

[56] References Cited

U.S. PATENT DOCUMENTS

| | | | |
|---|---|---|---|
| 4,364,932 | 12/1982 | Kung et al. | 530/387 |
| 4,364,937 | 12/1982 | Kung et al. | 530/387 |
| 4,381,292 | 4/1983 | Bieber et al. | 424/1.1 |
| 4,381,295 | 4/1983 | Kung et al. | 530/387 |
| 4,443,427 | 4/1984 | Reinherz et al. | 424/1.1 |
| 4,582,797 | 4/1986 | Trowbridge et al. | 530/387 |
| 4,624,925 | 11/1986 | Kung et al. | 435/240.27 |
| 4,710,457 | 12/1987 | Dupont et al. | 435/7.24 |

OTHER PUBLICATIONS

Peschel et al., "M7 Cluster Rept: CD34," ed. Knapp, at the Fourth Int'l Workshop and Conference on Human Leucocyte (1989), p. 817.

Civin et al., "M7.1 Rept on the CD34 Cluster Workshop," ed. Knapp, at the Fourth Int'l Workshop and Conference on Human Leucocyte (1989), p. 818.

Lansdrop et al., "M7.2 CD34 Epitopes," ed. Knapp, at the Fourth Int'l Workshop and Conference on Human Leucocyte (1989), p. 826.

Molgaard et al., "M7.3 Molecular Characterization of Human and Murine CD34," ed. Kanpp, at the Fourth Int'l Workshop and Conference on Human Leucocyte (1989), p. 827.

Civin et al., "Antigenic Analysis of Hematopoiesis III. A Hematopoietic Progenitor Cell Surface Antigen Defined by a Monoclonal Antibody Raised Against KG-1a Cells," J. Immunology 133:157-165 (1984).

Civin et al., "Cell Surface Antigens of Human Myeloid Cells", (1982) Exp. Hematol. 10:129 (abstract).

Civin et al., "Characterization of Four Monoclonal Antibodies Reactive with Human Cell Subsets," Blood, 60(5):95a (abstract).

Civin et al., "Cell Surface Antigens by Four Monoclonal Antibodies Raised Against KG-1a Cells," Hybridoma, 2:125a (abstract).

Brovall et al., "Identification and Partially Characterization of Two Human Potential Hematopoietic Differentiation Antigens" Exp. Hematol. 11:(Supp.) 199 (abstract).

Civin et al., "Diagnostic and Prognostic Utility of Cell Surface Markers In Acute Non-Lymphocytic Leukemia (ANLL)," Exp. Hematol. 11:(Supp.)84.

Strauss et al., "MY-10, A Human Hematopoietic Progenitor Cell Surface Antigen Identified by a Monoclonal Antibody" Exp. Hematol. 11:205 (abstract).

Strauss, et al. "MY-10 Antigen is Lost at the CFU-E Stage During Erythroid Progenitor Cell Maturation," (1984) I.S.E.H. (Abstract).

Leary, et al., "Single Cell Origin of Human Multilineage Colonies," (1984) I.S.E.H. (Abstract).

Bodger, et al., "Surface Antigenic Determinants on Human Pluripotent and Unipotent Hematopoietic Progenitor Cells," (1983) Blood, 61:1006-1010.

Bodger, et al., "A Monoclonal Antibody Specific for Immature Human Hemopoietic Cells and T Lineage Cells," (1981) J. Immunology, 127:2269-2274.

Nadler et al., "Diagnosis and Treatment of Human Leukemias and Lymphomas Utilizing Monoclonal Antibodies" Prog. Hematol., 12:187-225.

Winchester, et al., "Expression of Ia-like antigen molecules on human granulocytes during early phases of differentiation," Proc. Natl. Acad. Sci. USA 74:4012–4016 (1977).

Stashenko, et al., "Characterization of a Human B Lymphocyte-Specific Antigen" J. Immunology, 125:1678–1685 (1980).

Reinherz, et al., "Regulation of the Immune Response—Inducer and Suppressor T-Lymphocyte Subsets in Human Beings" (1980) N. Engl. J. Med. 303:370.

Ritz, et al., "A Monoclonal Antibody to Human Acute Lymphoblastic Leukaemia Antigen" Nature 283:583–585.

Price et al., "Characterization of Stem Cells and Progenitor of Hemampoiesis by Cell Sorting," *Blood Cells,* 5:161–169 (1979).

Miller et al., "Cell Surface Markers," *Clinics in Hematology,* 8:421–431 (1979).

Price et al., "Regulatory Receptors and Distinctive Surface Markers," *Blood Cells,* 6:689–696 (1980).

Castagnola et al., "Purification of Rat Pluripotent Hemopoietic Stem Cells," *Stem Cells,* 1:250 (1981).

Uchanska-Ziegler, "Monoclonal Antibodies Against Human Lymphoid and Myeloid Antigens: AMML Cells as Immunogen" in Knapp, Editor *Leukemia Markers,* 1981, p. 243.

Tindle et al., "A Novel Monoclonal Antibody BI-3CS Recognizes Myeloblasts and Non-B and Non-T Lymphoblasts in Acute Leukemias and CGL Blast Crises, and Reacts with Immature Cells in Normal Bone Marrow," *Leukemia Res.,* 9:1–9 (1985).

Beverley, et al., "Isolation of human hematopoietic progenitor cells using monoclonal antibodies," Macmillan Journals Ltd., 1980, 287:332–333.

Fukuda, et al., "Membrane differentiation in human myeloid cells: Expression of unique profiles of cell surface glycoproteins in myeloid leukemic cell lines blocked at different stages of differentiation and maturation," Proc. Natl. Acad. Sci., 1981, 78:6299–6303.

Strauss, et al., "Antigenic Analysis of Haematopoiesis. v. Characterization of My-10 Antigen Expression of Normal Lymphohematopoietic Progenitor Cells," Exp. Hematol, 1986, 14:878–886.

Basch, et al., "Cell Separation Using Positive Immunoselective Techniques," Journal of Immunol. Methods, 1983, 56:269–280.

Gee, et al., "Purging Tumor Cells From Bone Marrow by Use of Antibody and Complement: A Critical Appraisal," Journal of the National Cancer Institute, 1988, 80:145–154–159.

Bodger, et al., "A Monoclonal Antibody Specific For Immature Human Hemopoietic Cells And T Lineage Cells," The American Association of Immunologists, 1981, 127:2269–2274.

Morgan, et al., "Successful haplodentical mismatched bone marrow transplantation in severe combined immunodeficiency: T cell removal using CAMPATH-I monoclonal antibody and E-rosetting," British Journal of Haematology, 1986, 62:421–430.

Bodger, et al., "Surface Antigenic Determinants on Human Pluripotent and Unipotent Hematopoietic Progenitor Cells," Blood, 1983, 61:1006–1010.

Civin, et al., "Characterization of Four Monoclonal Antibodies Reactive With Human Cell Subsets," Blood, 1982, 60:95a, Abst. No. 307.

Young, et al., "Anti-K562 cell monoclonal antibodies recognize hematopoietic progenitors," Proc. Natl. Acad. Sci., 1981, 78:7073–7077.

Berenson et al., "Stem Cell Selection-Clinical Experience," in Bone Marrow Purging and Processing, published by Alan R. Liss, Inc., pp. 403–413 (1990).

Amato, et al., "Review of Bone Marrow Transplants at the Ontario Cancer Institute," Transplantation Today, 1971, 3:397–399.

*Primary Examiner*—Suzanne E. Ziska

[57] ABSTRACT

Monoclonal antibodies that recognize a stage-specific antigen on immature human marrow cells are provided. These antibodies are useful in methods of isolating cell suspensions from human blood and marrow that can be employed in bone marrow transplantation. Cell suspensions containing human pluripotent lympho-hematopoietic stem cells are also provided, as well as theraputic methods employing the cell suspensions.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *